(12) United States Patent
Salama

(10) Patent No.: US 7,749,534 B2
(45) Date of Patent: Jul. 6, 2010

(54) PHARMACEUTICAL COMPOSITION COMPRISING OXOPLATIN, THE SALTS AND DERIVATIVES THEREOF

(75) Inventor: Zoser B. Salama, Berlin (DE)

(73) Assignee: Riemser Arzneimittel AG (DE)

( * ) Notice: Subject to any disclaimer, the term of this patent is extended or adjusted under 35 U.S.C. 154(b) by 704 days.

(21) Appl. No.: 10/595,399

(22) PCT Filed: Oct. 13, 2004

(86) PCT No.: PCT/DE2004/002297

§ 371 (c)(1),
(2), (4) Date: Apr. 13, 2006

(87) PCT Pub. No.: WO2005/039605

PCT Pub. Date: May 6, 2005

(65) Prior Publication Data

US 2007/0048363 A1 Mar. 1, 2007

Related U.S. Application Data

(60) Provisional application No. 60/512,083, filed on Oct. 20, 2003.

(30) Foreign Application Priority Data

Oct. 13, 2003 (EP) .................................. 03090343

(51) Int. Cl.
*A61K 9/20* (2006.01)
*A61K 9/48* (2006.01)
(52) U.S. Cl. ........................ 424/465; 424/451; 424/452; 424/464
(58) Field of Classification Search .................. None
See application file for complete search history.

(56) References Cited

U.S. PATENT DOCUMENTS

| 4,119,653 | A |   | 10/1978 | Tobe et al. |  |
|---|---|---|---|---|---|
| 4,658,048 | A | * | 4/1987 | Totani et al. | 556/137 |
| 5,272,137 | A | * | 12/1993 | Blase et al. | 514/54 |
| 5,393,909 | A | * | 2/1995 | Khokhar et al. | 556/137 |
| 6,008,395 | A | * | 12/1999 | Kidani | 556/137 |
| 6,534,070 | B1 | * | 3/2003 | Franke et al. | 424/401 |
| 2003/0064494 | A1 | * | 4/2003 | Kumar et al. | 435/189 |
| 2004/0001801 | A1 | * | 1/2004 | Madison et al. | 424/85.1 |
| 2006/0258656 | A1 | * | 11/2006 | Matteucci et al. | 514/235.5 |
| 2007/0286905 | A1 |   | 12/2007 | Salama |  |

FOREIGN PATENT DOCUMENTS

| EP | 0339772 | 11/1989 |
|---|---|---|
| RU | 2086261 | 8/1997 |
| WO | WO 03/066526 | 8/2003 |

OTHER PUBLICATIONS

Database WPI, Section CH, Week 199815, Derwent Publications Ltd., London, GB; AN 1998-167679.
Tobe, M.L., et al., "Structure, activity, reactivity and solubility relationships of platinum diamine complexes", J.Clin.Hematol.Oncol. 1977, vol. 7, No. 1,1977, pp. 114-137.
Presnov, M.A., et al., "The antitumor activity of oxoplatinum", Neoplasma (1985), 32(1), pp. 73-83, 1985.
Presnov, M.A., et al., "Antitumor properties of cis-dichlorodiam-minedihydroxyplatinum(IV)", Izvestiya Akademii Nauk SSSR, Seriya Biologicheskaya (1986), (3), pp. 417-428, 1986.
Orr, R.M., et al., "Evaluation of novel platinum (II), and platinum (IV) amminelamine complexes in L 1210 murine leukemia cell lines sensitive and resistant to cisplatin and tetraplatin", Cellular Pharmacology (1993),1(1), pp. 17-23, 1993.
Brandon, R.J., et al., "Synthesis, characterization, and properties of a group of platinum (IV) complexes.", Journal of Medicinal Chemistry. United States Jul. 1984, vol. 27, No. 7, Jul. 1984, pp. 861-865.
Presnov, MA, et al., "Cycloplatam and oxoplatin—the new antitumor platinum compounds of the second generation", Arch IV Fuer Geschwulstforschung (1988), 58(1) pp. 43-49, 1988.
Kelland, L.R., et al., "Structure-activity relationships in a series of novel platinum(II) and platinum(IV) ammine-amine complexes evaluated against a panel of human ovarian carcinoma cell lines", Journal of Cellular Pharmacology (1991),2(1), pp. 331-342.
Giandomenico, C.M.. et al.. "Carboxylation of kinetically inert platinum(IV) hydroxy complexes. An entree into orally active platinum(IV) antitumor agents". Metal Construction. Cambridge. GB. vol. 34. 1995, pp. 1015-1021.
Blatter, E.E., et al., "Interaction of the antitumor agents cis,cis,trans-PtIV(NH3)2C12(OH)2 and cis,cis,trans-PtIV'(CH3)2CHNH2!2C12(OH)2 and their reduction products with PM2 DNA.", Biochemistry. United States Oct. 9, 1984, vol. 23, No. 21, pp. 4817-4820.
Keprtova, J., et al., "The effect of second generation platinum cytostatics on mammalian cell proliferation.", Neoplasma. Czechoslovakia 1990, vol. 37, No. 2,1990, pp. 121-129.
Yen, Tran Cong, et al., "Study on potential of prolongation of survival in mice with cancers (before and after amputation) treated with cis-dichlorodiamine trans-dihydroxo platinum(IV)", Tap Chi Duoc Hoc (2001), (2), pp. 19-21,2001.
Yen, Tran Cong, et al., "Action of platinum(IV) complexes on sarcoma TG-180 cells in vivo", Tap Chi Duoc Hoc (1998), (6), pp. 18-20,1998.

(Continued)

*Primary Examiner*—S. Tran
(74) *Attorney, Agent, or Firm*—Joyce von Natzmer; Pequignot + Myers

(57) ABSTRACT

The invention relates to a pharmaceutical agent, particularly a chemotherapeutical agent, comprising cis-diammonium-dichloro-trans-dihydroxoplatinum(IV) or salts and/or derivatives thereof in the form of capsules, tablets, creams, ointments and infusion solutions, and to the production of said pharmaceutical agent; the invention also relates to the use of such pharmaceutical agents in the treatment of tumor diseases.

7 Claims, No Drawings

OTHER PUBLICATIONS

Nguyen. Thi Quy. et al., "The antitumor effectiveness of a platinum(IV) compound in Swiss mice". Tap Chi Duoc Hoc (1998). (3), pp. 21-23.1998.

Arefeva, A.K., et al.. "Antitumor effectiveness and nephrotoxicity of oxoplatinum!" Voprosy Onkologii. USSR 1990. vol. 36, No. 3. 1990. pp. 331-334.

Kelland, L.R.. et al.. A novel trans-platinum coordination complex possessing in vitro and in vivo antitumor activity . . . Cancer Research. United States Nov. 1, 1994. vol. 54, No. 21. pp. 5618-5622.

Vollano. J.F., et al., "DNA breakage by a perhydrate complex of cis,cis.trans-PtIVCL2(NH3)2(OH)2", Journal of the American Chemical Society, XX, vol. 106. No. 9, 1984, pp. 2732-2733.

Novakova, Olga, et al.. "DNA interactions of antitumor platinum(IV) complexes", European Journal of Biochemistry (1995).228(3), pp. 616-624.1995.

Brabec, V.. et al., "Tetravalent platinum complexes can exert their antitumor effect via direct reaction with DNA", Studia Biophysica, vol. 114, No. 1-3, 1986. pp. 199-207.

Gutsche, W., et al.. "Structure-activity relationships of active antineoplastic platinum(II) and (IV) coordination compounds". Archiv Fuer Geschwulstforschung (1989). 59(4), pp. 233-238. 1989.

Presnov, M.A., et al., "Cycloplatam and oxoplatin—the new antitumor platinum compounds of the second generation", Archiv Fuer Geschwulstforschung (1988), 58(1) pp. 43-49, 1988.

Nguyen, Thi Quy, et al., "The antitumor effectiveness of a platinum(IV) compound in Swiss mice", Tap Chi Duoc Hoc (1998), (3), pp. 21-23, 1998.

Aref'eva, A.K., et al., "Antitumor effectiveness and nephrotoxicity of oxoplatinum!" Voprosy Onkologii. USSR 1990, vol. 36, No. 3, 1990, pp. 331-334.

Kelland, L.R., et al., "A novel trans-platinum coordination complex possessing in vitro and in vivo antitumor activity.", Cancer Research. United States Nov. 1, 1994, vol. 54, No. 21, pp. 5618-5622.

Vollano, J.F., et al., "DNA breakage by a perhydrate complex of cis,cis,trans-PtIVCL2(NH3)2(OH)2", Journal of the American Chemical Society, XX, vol. 106, No. 9, 1984, pp. 2732-2733.

Novakova, Olga, et al., "DNA interactions of antitumor platinum(IV) complexes", European Journal of Biochemistry (1995), 228(3), pp. 616-624, 1995.

Brabec, V., et al., "Tetravalent platinum complexes can exert their antitumor effect via direct reaction with DNA", Studia Biophysica, vol. 114, No. 1-3, 1986, pp. 199-207.

Gutsche, W., et al., "Structure-activity relationships of active antineoplastic platinum(II) and (IV) coordination compounds", Archiv Fuer Geschwulstforschung (1989), 59(4), pp. 233-238, 1989.

Giandomenico, C.M., et al., "Carboxylation of kinetically inert platinum(IV) hydroxy complexes. An entree into orally active platinum(IV) antitumor agents", Metal Construction, Cambridge, GB, vol. 34, 1995, pp. 1015-1021.

Notification of Requisition issued by the Canadian Intellectual Property Office on Jan. 21, 2010 in Canadian application No. 2,565,097.

Presnov, M.A., et al., "Antitumor properties of cis-dichlorodiamminedihydroxyplatinum(IV)", Izvestiya Akademii Nauk SSSR, Seriya Biologicheskaya (1986), (3), pp. 417-28, 1986.

Presnov, M.A., et al., "Cycloplatam and oxoplatin - the new antitumor platinum compounds of the second generation", Archiv Fuer Geschwulstforschung (1988), 58(1) pp. 43-9, 1988.

Keprtova, J., et al., "The effect of second generation platinum cytostatics on mammalian cell proliferation.", Neoplasma. Czechoslovakia 1990, vol. 37, No. 2, 1990, pp. 121-129.

Konovalova, A.L., et al., "Antineoplastic effect of complex platinum(IV) compounds", Doklady Akademii Nauk SSSR (1977), 234(1), pp. 223-6 'Biochem.!, 1977.

Yen, Tran Cong, et al., "Study on potential of prolongation of survival in mice with cancers (before and after amputation) treated with cis-dichlorodiamine trans-dihydroxo platinum(IV)", TAP CHI DUOC HOC (2001), (2), pp. 19-21, 2001.

Tran, Cong Yen, et al., "Action of platinum(IV) complexes on sarcoma TG-180 cells in vivo", TAP CHI DUOC HOC (1998), (6), pp. 18-20, 1998.

* cited by examiner

PHARMACEUTICAL COMPOSITION COMPRISING OXOPLATIN, THE SALTS AND DERIVATIVES THEREOF

This is the U.S. national stage of International application PCT/DE2004/002297, filed Oct. 13, 2004 designating the United States and claiming priority to European application EP03090343.9, filed Oct. 13, 2003 and U.S. provisional application 60/512,083, filed Oct. 20, 2003.

FIELD OF THE INVENTION

The invention relates to a pharmaceutical kit comprising cis-diammoniumdichloro-trans-dihydroxoplatinum(IV) and, separated therefrom, a pharmaceutical base material in the form of capsules, tablets, creams, ointments and infusion solutions, and to the production of such pharmaceutical agents; the invention also relates to the use of said pharmaceutical agents for the treatment of tumor diseases.

BACKGROUND OF THE INVENTION

Cancer is uncontrolled growth of new tissue, which is caused by degeneration of endogenic cells. Cancer cells are capable of invading other tissues and can destroy the latter. The main groups of cancerous diseases or tumor diseases include sarcomas, carcinomas, leukemias and lymphomas. The most frequent causes of death in industrial societies include cancerous and tumor diseases. For this reason, there have been great efforts of developing therapies for the treatment of cancerous diseases. However, many of these methods of treatment have been successful only in part. On the one hand, a tumor having already established in the body is difficult to combat in an organism by means of well-known agents, and, on the other hand, the antitumor agents being used generally show a large number of undesirable side effects, limiting in particular the dosage of agents to be administered.

In addition to gene-therapeutic approaches for the treatment of cancerous diseases, selected metals or metal compounds, e.g. of vanadium, molybdenum, gold and, in particular, platinum, have been used in the treatment of various tumor diseases for years. Apart from general side effects, a large number of the above-mentioned compounds being employed, e.g. platinum compounds, have a high toxic potential, and more specifically, these compounds are nephrotoxic. Furthermore, platinum compounds such as cis-platinum compounds show specific undesirable side effects, e.g. severe diarrhea, serious vomiting, loss of body hair, especially hair of the head. Furthermore, the activity—especially the immunologic activity—of the bone marrow is suppressed.

As a result of all this, patients—despite the threatening disease they experience—would prematurely break off this type of therapy and select other forms of therapy in order to treat their pathogenic condition.

As can be seen in cancer therapies in total, patients to be treated approve orally administered agents. An oral chemotherapy, for example, is very well accepted by patients owing to the fact that normal life can be continued, and that such treatments show relatively few side effects. In 2001, about 25 to 30% of the medications used in oncology were oral formulations. These oral formulations are conditionally suitable for the treatment of various disease-related mechanisms. Well-known examples of oral antitumor therapies are e.g. administration of cytotoxic agents, anti-angiogenesis products, agents modifying the cell cycle mechanisms, inhibitors of signal transduction, and hormone suppressants.

As a result of said good acceptance of oral chemotherapeutic agents, a number of attempts have been made in the prior art in order to provide pharmaceutical agents to be applied on the oral route, which would have good antitumor activity in combination with low toxicity. For this reason, there have been a number of attempts of providing pharmaceutical agents based on molybdenum, vanadium, gold, and especially platinum components, which have effective activity and few side effects. Well-known chemotherapeutic agents are highly toxic, therefore involving some risk in handling during shipping, delivery and storage.

A number of oxoplatinum (cis-oxoplatinum) compounds are well-known as tumor-influencing agents, comprising e.g. cis-diammoniumdichloro-trans-dihydroxoplatinum(IV) in buffer or NaCl solutions, which are applied in laboratory animals. There are no or few disclosures in the prior art as to pharmaceutical-technical formulations that could be used in humans. As is well-known, the pharmaceutical-technical formulation has an influence on the effect in human or animal patients. The prior art fails to provide data on particular compositions of pharmaceutical-technical base materials enabling effective activity of cis-oxoplatinum in living organisms.

To date, there has been no success in providing pharmaceutical agents to be used orally, especially chemotherapeutically usable compounds based on platinum compounds, which have low toxic activity, especially nephrotoxic activity. Furthermore, it has not been possible as yet to develop pharmaceutical agents comprising platinum, which could be accepted by patients and could be used e.g. as creams or ointments, especially for the treatment of tumor diseases of the skin.

The object of the invention was therefore to provide chemotherapeutical agents in a form that would not have the above-mentioned drawbacks, the oxoplatinum compound being used having low toxicity, especially nephrotoxicity, being well suited for use as oral agent or as a cream or ointment in tumor therapy, said oxoplatinum compound being incorporated in a well-defined pharmaceutical-technical formulation which allows safe and efficient effect of the oxoplatinum as a chemotherapeutical agent.

SUMMARY OF THE INVENTION

Said object according to the invention is accomplished by the present invention by means of a kit comprising cis-diammoniumdichloro-trans-dihydroxoplatinum(IV) (cis-oxoplatinum, oxoplatin), particularly salts thereof, and, physically separated therefrom, a base material of a pharmaceutical agent selected from the group comprising a tablet, a capsule, a coated tablet, a suppository, an ointment, a cream, a solution for infusion and/or injection, and optionally information relating to contacting or combining the contents of the kit, said base materials being selected in such a way that, following contacting or combining the cis-diammoniumdichloro-trans-dihydroxoplatinum(IV) with the base material, the capsule comprises oxoplatin:silicon dioxide:mannitol or magnesium stearate at a ratio of 0.1 to 10 :0.1 to 10 :0.1 to 10;

the tablet comprises cis-oxoplatin:lactose:corn starch:poly (O-carboxymethyl)starch sodium salt:calcium hydrogen phosphate×2H$_2$O:cellulose powder:magnesium stearate at a ratio of 10 to 500:20 to 150:1 to 10:1 to 10:1 to 10:1 to 10:0.1 to 7;or the tablet alternatively comprises cis-oxoplatin:silicon dioxide:magnesium stearate at a ratio of 0.1 to 10:0.1 to 10:0.1 to 10;

the cream comprises cis-oxoplatin:benzyl alcohol:cetyl stearyl alcohol:Macrogol stearate 1000:isopropyl palmitate:glycerol:70% sorbitol solution water at a ratio of 0.2 to 8:0.1 to 7:1 to 10:0.1 to 7:0.1 to 7:0.2 to 8:0.2 to 8:20 to 60;

the ointment comprises cis-oxoplatin:propylene glycol:Macrogol stearate 1000:cetyl stearyl alcohol:VASELINE retrolatum at a ratio of 2 to 20:5 to 40:0.1 to 7:1 to 10:25 to 400;

the gel comprises cis-oxoplatin:hydroxyethylcellulose:chlorocresol:sodium hydroxide:sodium hydrogen phosphate dihydrate:water at a ratio of 2 to 20:100 to 600:5 to 40:0.1 to 7:20 to 60:3,000 to 50,000;

the suppository comprises cis-oxoplatin:silicon dioxide:hardened fat at a ratio of 0.1 to 10:0.1 to 10:30 to 300; or the suppository alternatively comprises cis-oxoplatin:lactose:corn starch:adipic acid sodium:hydrogen carbonate:stearic acid:magnesium stearate:highly dispersed silicon dioxide:Polysorbate 80 at a ratio of 10 to 100:700 to 4,000:200 to 600:10 to 1000:10 to 1,000:1 to 100:1 to 100:1 to 15:0.1 to 10; or the suppository alternatively comprises cis-oxoplatin:lactose×1H$_2$O:corn starch:adipic acid:sodium hydrogen carbonate:stearic acid:magnesium stearate:silicon dioxide:Polysorbate 80 at a ratio of 10 to 100:1,000 to 5,000:300 to 1,000:100 to 1,000:10 to 1,000:1 to 100:1 to 100:1 to 15:0.1 to 7;or the suppository alternatively comprises cis-oxoplatin:lactose×1H$_2$O:corn starch:adipic acid:sodium hydrogen carbonate:stearic acid:magnesium stearate:silicon dioxide:Polysorbate 80 at a ratio of 10 to 1,000 :1,500 to 5,000:300 to 1,000:10 to 1,000:10 to 1,000:1 to 100:1 to 100:1 to 15:0.1 to 7:

the solution for injection or infusion comprises cis-oxoplatin:benzyl alcohol:Polysorbate 80:70% sorbitol solution:water at a ratio of 0.2 to 8 :1 to 10 :0.1 to 7 :100 to 800 :100 to 400; or the solution for injection or infusion alternatively comprises cis-oxoplatin:mannitol:water at a ratio of 0.1 to 7:5 to 40 :1 to 10.

Surprisingly, it was possible to demonstrate that physical separation in the kit of cis-diammoniumdichloro-trans-dihydroxoplatinum(IV) and pharmaceutical-technical base material, i.e., tablet, capsule, coated tablet, suppository, ointment, cream, solution for infusion and/or injection with no cis-diammoniumdichloro-trans-dihydroxoplatinum(IV), results in easier and safer handling of the chemotherapeutical agent to be produced and obtained from the components of the kit by contacting, e.g. mixing, compared to well-known agents.

Prior to use in a patient, the cis-diammoniumdichloro-trans-dihydroxoplatinum(IV) and the base material of the tablet, capsule, coated tablet, suppository, ointment, cream, solution for infusion and/or injection, i.e., the pharmaceutical-technical carrier with no cis-diammoniumdichloro-trans-dihydroxoplatinum(IV), are mixed together so as to provide a pharmaceutical agent for the treatment of tumors.

In contrast to conventional agents comprising toxic oxoplatin or cis-oxoplatinum, a kit wherein oxoplatin or cis-oxoplatinum and the pharmaceutical base material or carrier are present separated from each other is safer in handling. An agent, e.g. an infusion solution, which comprises oxoplatinum and base material already prior to use, i.e., during storage and shipping, has a toxic substance during the entire period of shipping and storage—in the present example in the form of a larger infusion solution. Such large-volume toxic agents are more difficult to handle compared to small concentrated amounts of oxoplatin, because small quantities can be stored in ampoules or in safe small-volume safety containers. Up to now, it has been assumed that incorporation of oxoplatin in the base material by mixing, prior to application in a patient, would not result in a pharmaceutical agent that could be handled safely, because e.g. mixing is poor because sufficient mixing without the use of industrial means is not possible. However, it has been found that standard laboratory apparatus available in clinics and research facilities are sufficient for this purpose, or that clinical dispensaries have the required apparatus available, or that usual manipulations during mixing by the clinical personnel or by the patient are sufficient to achieve the desired results in providing the chemotherapeutical agent from the components of the kit. More surprisingly, the use of said well-defined base materials for tablets, capsules, coated tablets, suppositories, ointments, creams, solutions for infusion and/or injection as carriers for cis-oxoplatinum results in a safe and efficiently effective drug. The base materials defined according to the invention allow safe provision of the drug by combining the components of the kit.

To improve the effect of a drug and reduce side effects, it is advantageous to transport the drug (oxoplatin) at elevated concentration to the site where effect is to take place and allow arrival at sites of possible side effects only with massively reduced concentration. According to the invention, this is accomplished by coupling oxoplatin to the carrier materials defined according to the invention, by means of which favorable distribution in the body is possible. Advantageously, such carriers recognize the site of action, liberating the oxoplatin active substance there.

Owing to the controlled release by means of the carriers according to the invention, it is possible to achieve a more uniform effect and, at the same time, extend the intervals between individual administrations or reduce the ingestion frequency. The administration form can be a tablet, but can also be a pad containing active substance, or an injection preparation. There are special techniques for each of the above-mentioned administration forms in order to liberate the active substance in a controlled fashion. A tablet, for example, remains in the gastro-intestinal tract for one day at maximum, and for this reason, prolongation of the release time of the active substance to more than one day is neither convenient nor taking place with the carriers defined according to the invention.

The production of the various drug forms requires co-processing of the active substances with adjuvants. Adjuvants must not have pharmacological activity by themselves, i.e., in particular, any toxicological risks must be excluded. At the same time, they must make sure that the active substance would stably remain in the final drug. Thus, the carriers defined according to the invention make sure that there be no chemical reactions between adjuvants and active substances.

One example addressing this field of problems and the associated considerations in the event of an injection solution in the form of an ampoule is as follows: if, as a result of good solubility and good stability of an active substance in water, a pure aqueous ampoule solution seems to be producible, it is necessary—depending on the tumor, i.e., the site of action—to consider and examine whether a solution defined according to the invention must be adjusted to a specific pH value or maintained constant (buffering).

Salts of cis-diammoniumdichloro-trans-dihydroxoplatinum(IV) or oxoplatin or cis-oxoplatin are preferred because of their surprisingly good water solubility which results in surprising advantages when administering the salts to an organism, e.g. in cases of gastric cancer or ophthalmic cancer. A pharmaceutical agent comprising cis-diammoniumdichloro-trans-dihydroxoplatinum(IV) and/or its salts or derivatives incorporated in the base materials defined according to the invention enables effective treatment of tumors. Surprisingly, it was found that pharmaceutical compounds comprising cis-diammoniumdichloro-trans-dihydroxoplatinum(IV) or cis-oxoplatin or oxoplatin and the base materials defined according to the invention have low toxic activity compared to e.g. cis-platinum compounds, and, in particular, they have little or no nephrotoxicity. Also, pharmaceutical agents comprising cis-oxoplatin and the base materials defined according to the invention have a shorter half-life in the body than comparable cis-platinum compounds; that is, the strain on important metabolic organs such as liver or kidneys caused by the compounds according to the invention is lower. Thus, for example, it was surprising to find that 20 days after injection of cis-oxoplatinum together with the injection solution of the invention the kidneys were largely free of said compound, whereas a comparative injection with cisplatin resulted in a level of platinum in the kidneys which was approximately as high as one hour following injection. In a particularly preferred fashion, salts are used, especially potassium, lithium, sodium, magnesium, barium, zinc, manganese, silver, copper, vanadium or calcium salts, wherein the anions can be e.g. chlorides, sulfates, phosphates, nitrates or carbonates or others. Other elements capable of forming salts are well-known to those skilled in the art, e.g. all elements from the main groups I to V of the Periodic Table of the Elements, as well as the elements from the subgroups I to VIII; all of the above-mentioned elements of the Periodic Table of the Elements can form cis-oxoplatinum salts.

For example, the derivatives can be alkyl and/or aryl derivatives wherein the positions of the cations and/or anions in the salts are formally occupied by alkyl and/or aryl residues. Preferred aryl residues are e.g. phenyl, naphthyl or anthryl residues, and preferred alkyl residues are e.g. methyl, ethyl or propyl residues.

Furthermore, the compounds of the invention obtained by combining the components of the kit show tendencies of biotransformation. That is, a pharmaceutical agent, particularly a chemotherapeutical agent, comprising cis-diammoniumdichloro-trans-dihydroxoplatinum(IV) is initially ingested e.g. on the oral route or in the form of an injection, and the latter acts efficiently against selected tumors, without exhibiting substantial toxic side effects, particularly when compared to cis-platinum compounds. After some time, the above platinum(IV) compound can be converted into a platinum(II) compound by processes inside the organism, which latter compound also has a specific effect against particular tumors. Advantageously, platinum(IV) and platinum(II) compounds may have different specificity in their antitumor activity.

Especially chemotherapeutical agents comprising salts of cis-diammoniumdichloro-trans-dihydroxoplatinum(IV) in the base materials defined according to the invention have very good solubility and therefore very good bioavailability. For this reason, they can be employed at lower concentration and nevertheless have higher effectiveness and less side effects compared to the corresponding base. Also, as a result of said good solubility, the salts are well suited for combinations with other active substances, vitamins, or other antitumor agents. In particular, the above salts readily dissolve in acid media such as those prevailing e.g. in a human or animal stomach. In contrast to the corresponding bases, the salts, once in contact with gastric acid, undergo dissolution much more readily and therefore can take effect immediately, e.g. in the stomach in case of a gastric tumor. Forming few adducts, the compounds of the invention are advantageously suited for the gastro-intestinal passage in particular. However, such reduced generation of adducts is not restricted to regions of the digestive tract, but also relates to the behavior of the inventive compounds in kidneys and liver. In the meaning of the invention, adducts are understood to be hazardous products high in side effects, which may result from degradation and rearrangement of the compounds according to the invention inside an organism.

Contacting can be performed by mixing, dispersing, compacting, compressing or grinding. Mixing is preferably effected by stirring, solid mixing, rolling, kneading, emulsifying, suspending, dissolving, exposure to ultrasound, etc. as dry, moist and wet mixing, depending on the state of matter and on the properties of the components to be mixed. In principle, the mixing apparatus (mixers) can be classified in static and dynamic mixers. While the former act by turbulence generated in liquids by specially shaped constructions during flow, said turbulence is actively generated in dynamic mixers. For example, types of mixers are impeller, turbo, blade, trough, planetary, attrition, screw, roll, centrifugal, countercurrent, jet, drum, conical, tumbling, rotary, cooling, vacuum, flow, gravity, fluid, and pneumatic mixers. More specifically, compacting can be effected using no binding agent or with addition of binding agents. In the meaning of the invention, dispersing is dividing of aggregates present in a filling agent, e.g. in the base material, in a liquid medium to form smaller particles and simultaneously wetting by the dispersing medium. Dispersing also includes random and even distribution of the particles generated in this way throughout the volume elements of the medium. The most important partial steps of dispersing can be summarized as follows: 1. wetting of the oxoplatin particles by the dispersing medium; 2. dividing of the agglomerates; and, optionally, 3. stabilization to prevent flocculation.

Preferred is a kit wherein the capsule additionally comprises silicon dioxide and mannitol or silicon dioxide and magnesium stearate and/or pharmaceutically acceptable vehicles, particularly siosomes, liposomes and/or nanocapsules.

Furthermore, a kit is preferred wherein the capsule, following contacting of cis-oxoplatin and base material, comprises 50 mg of silicon dioxide, 50 mg of mannitol or 50 mg of magnesium stearate and 50 mg of oxoplatin, or, alternatively, 50 mg of cis-oxoplatin, 39.5 mg of lactose or 39 mg, 2.5 mg or 2 mg of corn starch, 2.5 mg of poly(O-carboxymethyl) starch sodium salt, 2.5 mg of calcium hydrogen phosphate×2H$_2$O, 2.5 mg of cellulose powder, and 0.5 mg of magnesium stearate, or, alternatively, cis-oxoplatin, 50 mg of silicon dioxide and 50 mg of magnesium stearate. In another preferred kit, the cream, following contacting of cis-oxoplatin and base material, comprises 50 mg of cis-oxoplatin, 20 mg of benzyl alcohol, 100 mg of cetyl stearyl alcohol, 25 mg of Macrogol stearate 1000, 20 mg of isopropyl palmitate, 40 mg of glycerol, 50 mg of sorbitol, and 205 mg of water. Furthermore, a kit is preferred wherein the ointment, following contacting of cis-oxoplatin and base material, comprises 50 mg of cis-oxoplatin, 120 mg of propylene glycol, 5.5 mg of Macrogol stearate 1000, 22 mg of cetyl stearyl alcohol, and 851.5 mg of VASELINE petrolatum.

In another preferred kit, the gel, following contacting of cis-oxoplatin and base material, comprises 0.05 g of cis-oxoplatin, 1.8 g of hydroxyethylcellulose, 0.1 g of chloroaerosol, 0.005 g of sodium hydroxide, 0.17 g of sodium hydrogen phosphate dihydrate, and 97.875 g of water.

In still another preferred kit, the suppository, following contacting of cis-oxoplatin and base material, comprises 0.02 g of cis-oxoplatin, 0.02 g of silicon dioxide and 1.85 g of hardened fat; alternatively, the suppository comprises 20 mg of cis-oxoplatin, 1055 mg of lactose, 170 mg of corn starch, 63.60 mg of adipic acid, 50 mg of sodium hydrogen carbonate, 5 mg of stearic acid, 4.5 mg of magnesium stearate, 3 mg of highly dispersed silicon dioxide, and 0.5 mg of Polysorbate 80; alternatively, the suppository comprises 20 mg of cis-oxoplatin, 1350 mg of lactose×1H$_2$O, 170 mg of corn starch, 65 mg of adipic acid, 50 mg of sodium hydrogen carbonate, 5 mg of stearic acid, 4.5 mg of magnesium stearate, 3 mg of highly dispersed silicon dioxide, and 0.5 mg of Polysorbate 80, or, alternatively, the suppository comprises 50 mg of cis-oxoplatin, 1450 mg of lactose×1H$_2$O, 170 mg of corn starch, 65 mg of adipic acid, 50 mg of sodium hydrogen carbonate, 5 mg of stearic acid, 4.5 mg of magnesium stearate, 3 mg of highly dispersed silicon dioxide, and 0.5 mg of Polysorbate 80.

In yet another preferred kit, the preparation, following contacting of cis-oxoplatin and base material of a 5 mg/ml injection or infusion solution, comprises 5 mg of cis-oxoplatin, 9 mg of benzyl alcohol, 2 mg of Polysorbate 80, 650 mg of 70% sorbitol solution, and 500 mg of water.

The pharmaceutical agents according to the invention, which can be produced using said kit, are capable of binding directly to a DNA. The cis-platinum compounds according to the invention have an octahedral configuration. Consequently, cis-oxoplatin in the meaning of the invention can form both intra- and inter-strand DNA complexes. Due to the specific structure of cis-oxoplatin, in contrast to cisplatin, the compounds of the invention form multiple bonds with DNA strands. Owing to the inter-strand-crosslinker complexes and intra-strand-crosslinker complexes, the compounds of the invention show advantageous specific cytostatic effects in anti-tumor therapy. The DNA adducts of the compounds according to the invention show higher charge of the platinum central atom and further have two additional ligands bound to this center. Owing to the octahedral configuration of the platinum(IV) complexes according to the invention, highly specific, relatively slow DNA binding is possible, which shows a more efficient effect compared to e.g. binding of cisplatin with DNA. Another advantage is that cis-oxoplatin at comparable concentrations—unlike cisplatin—does not inhibit proteases such as trypsin or α-chymotrypsin. Potency and effectiveness of the inventive pharmaceutical agents comprising cis-oxo-platinum(IV) are largely independent of the form of application of the agents. The agents can be administered perorally, orally, rectally, subcutaneously, intramuscularly, intravenously and intraperitoneally. Compared to well-known cis-platinum compounds, the compounds of the invention are also advantageous in that the therapeutic effect of the compounds according to the invention lasts longer, and furthermore, the compounds of the invention are highly effective at various stages of tumor growth, and cis-oxoplatinum compounds show a longer lasting positive effect in therapy when compared to comparable cis-platinum compounds. These properties in solubility, pharmacogenetics, bioavailability, as well as degradation and absorption in the body allow more effective treatment of tumor diseases with the agents according to the invention as compared to well-known pharmaceutical agents comprising platinum.

In a preferred embodiment of the invention the pharmaceutical agent according to the invention, which is produced by combining the components of the kit, is a chemotherapeutical agent used in tumor prophylaxis and/or therapy. Tumor prophylaxis in the meaning of the invention means preventing the development of a tumor or inhibiting the growth or stopping the growth of single tumorous tissues, as well as preventing or reducing metastasizing of tumors, preventing or reducing the invasion of single tumor cells in surrounding tissue, as well as suppressing or inhibiting angiogenesis associated with tumor development. The chemotherapeutical agent can therefore be used in the prevention of tumors, e.g. in those cases where minor tumors are present, but also in prophylaxis to effect early termination of tumor development.

When using the agents according to the invention in prophylaxis, they can be employed as a vaccine. Various ways of formulating and generating vaccines, e.g. by selecting carriers or solvents, are well-known to those skilled in the art.

In a preferred fashion the chemotherapeutical agents are employed as capsules, tablets, creams, ointments, suppositories and/or infusion solutions. The chemotherapeutical agents can inhibit spreading and growth of cancer cells and other pathogens such as parasites, viruses, bacteria and others. For example, liver tumors caused by hepatitis viruses can be treated with the chemotherapeutical agents of the invention in such a way that the agent administered orally acts both on the hepatitis viruses and on the cancer cells induced thereby.

Capsules or tablets in the meaning of the invention are forms of application or administration which, in particular, allow oral ingestion by a patient. Tablets and capsules in the meaning of the invention also include other pharmaceutical agents allowing oral ingestion, such as coated tablets, pills and suppositories, as well as drops, syrups or fluid mixtures.

Suppositories in the meaning of the invention are all administration forms allowing e.g. rectal or vaginal uptake by the organism.

Tablets, coated tablets, capsules, pills, powders and suppositories are essentially solid drug forms. The above solid drug forms can merge into one another. Thus, for example, a tablet can disintegrate into a powder on the tongue during oral ingestion or release a solution, e.g. a syrup, incorporated therein. In addition to the actual active substance, the tablets according to the invention also comprise adjuvants or binding agents. For example, such adjuvants can be starch, mannitol, lactose, sugar, alcohols or calcium sulfate. The binding agents can be cellulose or mannitol, for example.

Tablets in the meaning of the invention can be film tablets, for example. Film tablets are tablets coated with a lacquer. Film tablets and coated tablets involve coating layer by layer in the form of solutions and subsequent drying. In particular, film tablets are used in those cases where the active substance according to the invention, namely, cis-diammonium-dichloro-trans-dihydroxoplatinum(IV), is intended to take effect at high concentration only after reaching the small intestine. Furthermore, the tablets can be press-coated tablets. Press-coated tablets involve coating one or more layers on the core in dry form using pressure. In this way, it is possible to accommodate in the press-coated tablets a combination of mutually incompatible active substances in a single preparation, i.e., in the core and coat. Obviously, this principle also applies to laminated tablets comprising cis-oxoplatin. Here, inventive tablets are concerned wherein layers having different release and dissolution properties are pressed one on top of the other. Furthermore, the press-coated tablets can be administered in the form of depot tablets and/or depot coated tablets. Using this form of application, it is possible, in particular, to maintain the required drug concentrations in an organism over a prolonged period of time. The production of film tablets and press-coated tablets is well-known to those skilled in the art. Other forms of application allowing oral ingestion in the meaning of the invention are capsules, pellets, powders and poudrages.

For example, capsules can be hard gelatin capsules containing single doses of the cis-oxoplatin compounds in an envelope of gelatin. However, it is also possible to use soft gelatin capsules holding the inventive active substances in liquid form, e.g. in the form of a solution or suspension. Apart from oral application, they can also be used for rectal and vaginal application. Also preferred is the use of hard gelatin plug-in capsules filled with about 300 pellets in the form of active substance granulate beads. Advantageously, substances or mixtures difficult to absorb or unstable to acid can be administered as a prodrug in this way. Advantageously, following dissolution of the surrounding hard gelatin capsules in the stomach, the small pellets are conveyed into the intestine, thus ensuring a constant absorption and constant concentration of cis-diammoniumdichloro-trans-dihydroxo-platinum(IV). The release of active substance and, as a consequence, the site and time profile of absorption can be controlled by means of suitable methods of producing the oral agents, which methods are well-known to those skilled in the art. The chemotherapeutical agents to be used orally can be coated with various films, e.g. films of wax, if release of the cis-oxoplatinum compounds is desired only after reaching the intestine. For example, this can be advantageous in some forms of intestinal cancer.

Apart from solid drug forms, particularly such as capsules, tablets and suppositories, non-solid drug forms can also be preferred. For example, this concerns ointments, creams and pastes which can be applied externally on the skin. In particular, this is advantageous in those cases where specific active substances are to be prevented explicitly from reaching the bloodstream; that is, if systemic absorption thereof is undesirable. This can be advantageous in some forms of skin cancer, for example. Of course, the ointments can also be prepared in such a way that the active substances can reach the tissue beneath the skin, part thereof reaching the vascular system. This concerns the absorption ointments well-known to those skilled in the art. To reach a site of action beneath the upper layers of the skin, as is required e.g. in the treatment of some melanomas, the cis-oxoplatin active substance advantageously can leave the formulation and penetrate the skin. More specifically, such penetration is necessary in those cases where a systemic effect is intended in addition to the topical effect. To this end, suppositories and transdermal therapeutic systems, such as nitrate pads, can be used, for example. A person skilled in the art will know how to provide such systems and administration forms. Thus, for example, the greater the difference in lipophilicity between the carrier and the active substance, the greater the tendency of an active substance of leaving the carrier.

For example, the ointments according to the invention are constituted of a lipophilic base, such as paraffin oil, VASELINE petrolatum and wool fat, and may include about 10% powder such as zinc oxide, titanium oxide, starch or another powder mixture. In hydrophobic ointments in the meaning of the invention, the outer phase is lipophilic, i.e., these ointments represent an emulsion of water in fat.

In particular, pastes in the meaning of the invention are fatty ointments having an amount of powdered components of at least 10%.

Creams in the meaning of the invention are preparations consisting of a lipophilic phase and a hydrophilic phase. In hydrophilic creams, the outer phase is the aqueous one, formed e.g. by means of emulsifiers as an emulsion of a fat in water.

In addition to the active substance, gels comprise gel-forming agents such as gelatin, methylcellulose and/or polyethylene glycol.

Among suppositories, administration forms of a torpedo-like shape are preferred, wherein the cis-oxoplatin active substance is uniformly distributed in a base mass, mostly neutral fats. For example, they are intended for insertion into the rectum or into the vagina to release the active substances therein by melting or dissolution. In a preferred fashion the suppositories are used to produce a local effect or absorb substances rectally or vaginally, e.g. in case of a tumor in the vaginal region or in case of a colon cancer. In particular, this is preferred in those cases where the patient shows a tendency of chronic nausea due to side effects of other antitumor agents, where liver passage immediately after absorption is to be avoided or rapid degradation is to be prevented. Advantageously, a major amount of the rectally absorbed cis-oxoplatinum compounds is directly supplied to the systemic circulation, thus evading the liver passage. In addition to vaginal suppositories, vaginal spheres (ovula) may also be preferred.

In the meaning of the invention, liquid administration forms can preferably be infusion solutions, but also syrups or fluid mixtures. For example, if a tumor of the tongue or a tumor of the upper neck region is to be treated, such solutions can be offered for gargling or washing. In particular, the syrups of the invention may include sugars and sugar substitutes with a sweet taste.

The injection and infusion solutions according to the invention are essentially free of infectious pathogens or suspended matter. Following production, the solutions for injection or infusion are sealed in an airtight fashion and stored in glass or plastic containers which can be colorless or, due to possible light sensitivity, provided with a brown color. In particular, oily formulations are used in those cases where subcutaneous or intramuscular depots are to be generated in an organism.

In a preferred embodiment of the invention the capsules according to the invention—in addition to said cis-oxoplatinum compounds—comprise silicon dioxide and mannitol or silicon dioxide and magnesium stearate or a mixture of lyophilized encapsulated or bound cis-oxoplatin on or in vehicles such as siosomes, liposomes and/or nanosomes. Advantageously, by selecting the above-mentioned pharmaceutical adjuvants and carriers, it is possible to make a selection as to whether the cis-oxoplatin active substance is liberated either rapidly or slowly after absorption in the organism.

The capsules according to the invention, especially those rapidly releasing the active substance, comprise cis-oxoplatin:silicon dioxide:mannitol or magnesium stearate preferably at a ratio of 0.1 to 10:0.1 to 10:0.1 to 10, more preferably 0.5 to 5:0.5 to 5:0.5 to 5, and even more preferably 0.7 to 2:0.7 to 2. 0.7 to 2, especially at a ratio of 1:1:1. Thus, for example, the capsule in the meaning of the invention may comprise 50 mg of silicon dioxide, 50 mg of mannitol, 50 mg of oxoplatin or 50 mg of magnesium stearate. Depending on the production process, such capsules are also suitable for slow release of the active substances. The selection of such production processes is well-known to those skilled in the art. Obviously, the capsules may also comprise lipid vehicles such as siosomes, liposomes, nanocapsules or nanosomes. By selecting the corresponding siosomes, liposomes and nanosomes, rapid or slow release of the cis-oxoplatin can be adjusted. As is well-known to those skilled in the art, it is possible to influence the liberation and absorption or uptake, the distribution, the degradation and elimination of the corresponding active substances and, in most cases, the entire complex of pharmacokinetics and pharmacodynamics of the chemotherapeutical agents according to the invention.

In addition to cis-oxoplatin, the tablet in a preferred embodiment of the invention comprises lactose, corn starch, poly(O-carboxymethyl)starch sodium salt, calcium hydrogen phosphate×2$H_2O$, cellulose powder and magnesium stearate or silicon dioxide and magnesium stearate.

In a distinctive embodiment the ratio of cis-oxoplatin:lactose:corn starch:poly(O-carboxymethyl)starch sodium salt:calcium hydrogen phosphate×2H$_2$O:cellulose powder:magnesium stearate is 10 to 500:20 to 150:1 to 10:1 to 10:1 to 10:1 to 10:0.1 to 7, preferably 20 to 200:40 to 100:2 to 8:2 to 8:2 to 8:2 to 8:0.5 to 5, and more preferably 50 to 150:60 to 90:3 to 7:3 to 7:3 to 7:3 to 7:0.7 to 1, especially 100:79:5:5:5:5:1.

Accordingly, an advantageous tablet includes, for example, 50 mg of cis-oxoplatin, 39.5 mg of lactose, 2.5 mg of corn starch, 2.5 mg of poly(O-carboxymethyl)starch sodium salt, 2.5 mg of calcium hydrogen phosphate×2H$_2$O, 2.5 mg of cellulose powder, and 0.5 mg of magnesium stearate. In a preferred fashion, such tablets are suitable for rapid release of the active substance. In another advantageous tablet in the meaning of the invention, 39 mg of lactose instead of 39.5 mg of lactose and 2 mg of corn starch instead of 2.5 mg of corn starch are employed per tablet, for example.

However, it may also be preferred to use tablets liberating the active substance very slowly. Such tablets comprise cis-oxoplatin:silicon dioxide:magnesium stearate preferably at a ratio of 0.1 to 10:0.1 to 10:0.1 to 10, more preferably 0.5 to 5:0.5 to 5:0.5 to 5, and even more preferably 0.7 to 2:0.7 to 2:0.7 to 2, especially 1:1:1. Accordingly, a tablet giving slow release of the active substances may comprise 50 mg of cis-oxoplatin, 50 mg of silicon dioxide and 50 mg of magnesium stearate.

Also preferred is the use of a cream which, in addition to cis-oxoplatin, comprises benzyl alcohol, cetyl stearyl alcohol, Macrogol stearate 1000, isopropyl palmitate, glycerol, sorbitol solution, preferably 70%, more preferably non-crystallizing, and purified water.

In a preferred variant of designing a cream according to the invention the ratio of cis-oxoplatin:benzyl alcohol:cetyl stearyl alcohol:Macrogol stearate 1000:isopropyl palmitate:glycerol:70% sorbitol solution:water is preferably 0.2 to 8:0.1 to 7:1 to 10:0.1 to 7:0.1 to 7:0.2 to 8:0.2 to 8:20 to 60, more preferably 0.4 to 4:0.2 to 3:2 to 9:0.2 to 3:0.2 to 3:0.4 to 4. 0.4 to 4:25 to 45, and even more preferably 0.7 to 3:0.5 to 1.5:4 to 6:0.5 to 1.5:0.5 to 1.5:0.7 to 3:0.7 to 3:30 to 40, especially 2.5:1:5:1.25:1:2:2.5:2.5:35.25. Accordingly, a preferred cream according to the invention is composed of 50 mg of cis-oxoplatin, 20 mg of benzyl alcohol, 100 mg of cetyl stearyl alcohol, 25 mg of Macrogol stearate 1000, 20 mg of isopropyl palmitate, 40 mg of glycerol, 50 mg of sorbitol, and 205 mg of purified water, for example.

When using the chemotherapeutical agent in the form of an ointment, it is preferred to use an ointment which, in addition to cis-oxoplatin, includes white VASELINE retrolatum, cetyl stearyl alcohol, Macrogol stearate 1000, and propylene glycol.

In a preferred embodiment of the invention the ointment includes the individual components cis-oxoplatin:propylene glycol:Macrogol stearate 1000:cetyl stearyl alcohol:white VASELINE retrolatum at a ratio of 2 to 20:5 to 40:0.1 to 7:1 to 10:25 to 400, preferably at a ratio of 5 to 12:10 to 30:0.2 to 3:2 to 9:50 to 250, and more preferably at a ratio of 6 to 10:15 to 25:0.5 to 1.5:3 to 6:100 to 200, and especially at a ratio of 9.1:22:1:4:155. Accordingly, the ointment according to the invention may comprise e.g. 50 mg of cis-oxoplatin, 120 mg of propylene glycol, 5.5 mg of Macrogol stearate 1000, 22 mg of cetyl stearyl alcohol, and 851.5 mg of white VASELINE petrolatum.

When used as a gel, especially as a mold gel, for topical application, such a gel preferably comprises hydroxyethylcellulose, chloroaerosol, sodium hydroxide, sodium hydrogen phosphate dihydrate and purified water.

In a preferred embodiment of the invention the mold gel comprises cis-oxoplatin:hydroxyethylcellulose:chloroaerosol:sodium hydroxide:sodium hydrogen phosphate dihydrate:purified water at a ratio of 2 to 20:100 to 600:5 to 40:0.1 to 7:20 to 60:3,000 to 50,000, preferably at a ratio of 4 to 18:200 to 500:10 to 30:0.2 to 3:25 to 45:5,000 to 35,000, and more preferably at a ratio of 6 to 12:300 to 400:15 to 25:0.5 to 1.5:30 to 40:10,000 to 30,000, and especially at a ratio of 10:360:20:1:34:19,569. Thus, for example, a mold gel may comprise 0.05 g of cis-oxoplatin, 1.8 g of hydroxyethylcellulose, 0.1 g of chloroaerosol, 0.005 g of sodium hydroxide, 0.17 g of sodium hydrogen phosphate dihydrate, and 97.875 g of purified water, so that 100 g of the preferred gel of the invention can be provided.

In another embodiment of the invention, it is preferred to use a suppository form, especially for anal or vaginal application, comprising highly dispersed silicon dioxide and hardened fat, or lactose, corn starch, adipic acid, sodium hydrogen carbonate, stearic acid, magnesium stearate, highly dispersed silicon dioxide and Polysorbate 80.

In a preferred embodiment of the invention the anal suppositories comprise cis-oxoplatin and highly dispersed silicon dioxide and hardened fat at a ratio of 0.1 to 10:0.1 to 10:30 to 300, preferably at a ratio of 0.2 to 4:0.2 to 4:40 to 200, more preferably at a ratio of 0.5 to 2:0.5 to 2:60 to 150, and especially at a ratio of 1:1:92.5; that is, such an application form may comprise e.g. 0.02 g of cis-oxoplatin, 0.02 g of highly dispersed silicon dioxide and 1.85 g of hardened fat. Another preferred suppository comprises cis-oxoplatin:lactose:corn starch:adipic acid:sodium hydrogen carbonate:stearic acid:magnesium stearate:highly dispersed silicon dioxide:Polysorbate 80 at a ratio of 10 to 100:700 to 4,000:200 to 600:10 to 1,000:10 to 1000:1 to 100:1 to 100:1 to 15:0.1 to 10, preferably at a ratio of 20 to 80:1,000 to 3,000:250 to 450:20 to 400:20 to 400:2 to 40:2 to 40:2 to 10:0.2 to 4, more preferably 30 to 60:1,500 to 2,500:300 to 400:50 to 200:50 to 200:5 to 20:5 to 20:4 to 8:0.5 to 2, and especially at a ratio of 40:2,111:340:127:100:10:9:6:1. Accordingly, a preferred anal suppository may comprise 20 mg of cis-oxoplatin, 1055, 40 mg of lactose, 170 mg of corn starch, 63.60 mg of adipic acid, 50 mg of sodium hydrogen carbonate, 5 mg of stearic acid, 4.5 mg of magnesium stearate, 3 mg of highly dispersed silicon dioxide, and 0.5 mg of Polysorbate 80.

Obviously, apart from the use in anal application, a vaginal application form can be preferred which, in a particularly preferred fashion, comprises lactose×1H$_2$O, corn starch, adipic acid, sodium hydrogen carbonate, stearic acid, magnesium stearate, highly dispersed silicon dioxide, and Polysorbate 80.

In a preferred embodiment of the invention a vaginal suppository comprises cis-oxoplatin:lactose×1H$_2$O:corn starch:adipic acid:sodium hydrogen carbonate:stearic acid:magnesium stearate:highly dispersed silicon dioxide:Polysorbate 80 at a ratio of 10 to 100:1,000 to 5,000:300 to 1,000:10 to 1,000:10 to 1,000:1 to 100:1 to 100:1 to 15:0.1 to 7, preferably at a ratio of 20 to 90:1,500 to 3,500:400 to 800:20 to 400:20 to 400:2 to 40:2 to 40:2 to 10:0.2 to 3, more preferably at a ratio of 30 to 60:2,000 to 3,000:500 to 600:50 to 200:50 to 200:5 to 20:5 to 20:4 to 8:0.5 to 1.5, and especially at a ratio of 40:2,700:567:130:100:10:9:6:1. In a preferred embodiment, for example, such a vaginal suppository may therefore comprise 20 mg of cis-oxoplatin, 1,350 mg of lactose×1H$_2$O, 170 mg of corn starch, 65 mg of adipic acid, 50 mg of sodium hydrogen carbonate, 5 mg of stearic acid, 4.5 mg of magnesium stearate, 3 mg of highly dispersed silicon dioxide, and 0.5 mg of Polysorbate 80.

Another preferred vaginal suppository comprises the same ingredients preferably at a ratio of 10 to 1,000:1,500 to 5,000: 300 to 1,000:10 to 1,000:10 to 1,000:1 to 100:1 to 100:1 to 15:0.1 to 7, more preferably at a ratio of 20 to 400:2,000 to 4,000:400 to 800:20 to 400:20 to 400:2 to 40:2 to 40:2 to 10:0.2 to 3, even more preferably at a ratio of 50 to 200:2,500 to 3,500:500 to 600:50 to 200:50 to 200:5 to 20:4 to 8:0.5 to 1.5, and especially at a ratio of 100:2,900:567:130:100:10:9: 6:1. Accordingly, such a suppository in a preferred embodiment may comprise 50 mg of cis-oxoplatin, 1,450 mg of lactose×1H$_2$O, 170 mg of corn starch, 65 mg of adipic acid, 50 mg of sodium hydrogen carbonate, 5 mg of stearic acid, 4.5 mg of magnesium stearate, 3 mg of highly dispersed silicon dioxide, and 0.5 mg of Polysorbate 80.

Of course, it may also be preferred to use the chemotherapeutical agent of the invention in the form of solutions for injection or infusion. In a preferred embodiment of the invention, an injection solution—apart from cis-oxoplatin—comprises benzyl alcohol, Polysorbate 80, sorbitol solution, preferably 70%, more preferably non-crystallizing, and water, or mannitol and water.

In a preferred embodiment of the invention the injection solution comprises cis-oxoplatin:benzyl alcohol:Polysorbate 80:70% sorbitol solution:water at a ratio of 0.2 to 8:1 to 10:0.1 to 7:100 to 800:100 to 400, preferably at a ratio of 0.4 to 4:2 to 9:0.2 to 3:200 to 600:150 to 350, more preferably at a ratio of 0.7 to 3:3 to 6:0.5 to 1.5:250 to 400:200 to 300, and especially at a ratio of 2.5:4.5:1:325:250. Accordingly, a preparation of a 5 mg/ml injection solution may include 5 mg of cis-oxoplatin, 9 mg of benzyl alcohol, 2 mg of Polysorbate 80, 650 mg of 70% sorbitol solution, and 500 mg of water.

Another preferred injection solution comprises cis-oxoplatin:mannitol:water at a ratio of 0.1 to 7:5 to 40:1 to 10, preferably at a ratio of 0.2 to 3:10 to 30:2 to 9, more preferably at a ratio of 0.5 to 1.5:15 to 25:3 to 6, and especially at a ratio of 1:20:4. Accordingly, a preparation of a 5 mg/ml injection solution may comprise 5 mg of cis-oxoplatin, 100 mg of mannitol and 200 ml of water for injection.

The invention also relates to the production of said capsules, tablets, suppositories, ointments, creams and/or infusion solutions. Depending on the release of active substance, e.g. in a spontaneous or time-shifted fashion or in the stomach or in the small intestine, the oral solid forms of application—as set forth above—may comprise particular wax layers, for example. A person skilled in the art will know how to provide solid oral forms or solid suppository forms or ointments, creams and powders or liquid infusion solutions by selecting particular parameters and selecting particular adjuvants. The production of individual forms of application may also depend on the type of tumor to be treated. Oral forms of application, such as tablets and capsules, for the treatment of intestinal or colon cancer are therefore coated with a gastric juice-resistant layer during production. Other forms of application are well-known to those skilled in the art, e.g. gel, poudrage, powder, tablet, sustained-release tablet, premix, emulsion, brew-up formulation, drops, concentrate, granulate, syrup, pellet, bolus, capsule, aerosol, spray and/or inhalant. These preparations can be employed orally, subcutaneously, intravenously, intramuscularly, intraperitoneally, vaginally, rectally, nasally and/or topically.

Thus, the invention relates to a method for the production of a chemotherapeutical agent, i.e. a pharmaceutical agent, in which method cis-diammoniumdichloro-trans-dihydroxoplatinum(IV) (cis-oxoplatin), and particularly the salts thereof, are contacted with a base material of a pharmaceutical agent selected from the group comprising a tablet, a capsule, a coated tablet, a suppository, an ointment, a cream, a solution for infusion and/or injection, said base materials being selected in such a way that, following contacting of cis-diammoniumdichloro-trans-dihydroxoplatinum(IV) with the base material,

- the capsule comprises oxoplatin:silicon dioxide:mannitol or magnesium stearate at a ratio of 0.1 to 10 :0.1 to 10:0.1 to 10;
- the tablet comprises cis-oxoplatin:lactose:corn starch:poly (O-carboxymethyl)starch sodium salt:calcium hydrogen phosphate×2H$_2$O:cellulose powder:magnesium stearate at a ratio of 10 to 500:20 to 150:1 to 10:1 to 10:1 to 10:1 to 10:0.1 to 7; or
- the tablet alternatively comprises cis-oxoplatin:silicon dioxide:magnesium stearate at a ratio of 0.1 to 10:0.1 to 10:0.1 to 10;
- the cream comprises cis-oxoplatin:benzyl alcohol:cetyl stearyl alcohol:Macrogol stearate 1000:isopropyl palmitate:glycerol:70% sorbitol solution:water at a ratio of 0.2 to 8:0.1 to 7:1 to 10:0.1 to 7:0.1 to 7:0.2 to 8:0.2 to 8:20 to 60;
- the ointment comprises cis-oxoplatin:propylene glycol: Macrogol stearate 1000:cetyl stearyl alcohol:VASELINE retrolatum at a ratio of 2 to 20:5 to 40:0.1 to 7:1 to 10:25 to 400;
- the gel comprises cis-oxoplatin:hydroxyethylcellulose: chloroaerosol:sodium hydroxide:sodium hydrogen phosphate dihydrate:water at a ratio of 2 to 20:100 to 600:5 to 40:0.1 to 7:20 to 60:3,000 to 50,000;
- the suppository comprises cis-oxoplatin:silicon dioxide: hardened fat at a ratio of 0.1 to 10:0.1 to 10:30 to 300; or
- the suppository alternatively comprises cis-oxoplatin:lactose:corn starch:adipic acid:sodium hydrogen carbonate:stearic acid:magnesium stearate:highly dispersed silicon dioxide:Polysorbate 80 at a ratio of 10 to 100:700 to 4,000:200 to 600:10 to 1000:10 to 1,000:1 to 100:1 to 100:1 to 15:0.1 to 10; or
- the suppository alternatively comprises cis-oxoplatin:lactose×1H$_2$O:corn starch:adipic acid:sodium hydrogen carbonate:stearic acid:magnesium stearate:silicon dioxide:Polysorbate 80 at a ratio of 10 to 100:1,000 to 5,000: 300 to 1,000:10 to 1,000:10 to 1,000:1 to 100:1 to 100 :1 to 15:0.1 to 7; or
- the suppository alternatively comprises cis-oxoplatin:lactose×1H$_2$O:corn starch:adipic acid:sodium hydrogen carbonate:stearic acid:magnesium stearate:silicon dioxide:Polysorbate 80 at a ratio of 10 to 1,000 :1,500 to 5,000:300 to 1,000:10 to 1,000:10 to 1,000:1 to 100:1 to 100:1 to 15:0.1 to 7:
- the solution for injection or infusion comprises cis-oxoplatin:benzyl alcohol:Polysorbate 80:70% sorbitol solution:water at a ratio of 0.2 to 8 :1 to 10 :0.1 to 7 :100 to 800 :100 to 400; or
- the solution for injection or infusion alternatively comprises cis-oxoplatin:mannitol:water at a ratio of 0.1 to 7:5 to 40 :1 to 10.

The invention also relates to the use of the pharmaceutical agent according to the invention in the treatment of tumors, and to the use of the agents of the invention, particularly of the kit, in the production of a drug for the treatment of tumors. Initially, the components of the kit are physically separated in the kit. To provide a chemotherapeutical agent, the base material(s)—as a component of the kit—is/are contacted with the oxoplatin—as another component of the kit—safely stored in the kit, thereby producing the chemotherapeutical agent. The preparation should be effected directly prior to use, i.e., minutes or hours prior to application in a patient. Of course, combining the contents of the kit is also possible markedly prior to use, e.g. some hours or one or more days before.

The treatment of tumors in the meaning of the invention comprises both prophylactic and therapeutic treatment of tumors. The pharmaceutical agent can be employed as a vaccine after tumor formation, or as a preventive vaccination. Advantageously, vaccination is effected in such a way that, following application, protection against spreading or formation of tumors is developed in the organism. Of course, it is also possible to effect vaccination immediately prior to or shortly after manifestation of a tumor, or as a therapy with a plurality of applications. Those skilled in the art are familiar with the fact that tumor treatment can be advantageous at virtually any point in time following formation of metastases, so that vaccination in the meaning of the invention could also be application of the inventive pharmaceutical agent weeks, months, years or decades after formation of a tumor. When using the pharmaceutical agents according to the invention as a therapeutic agent, one crucial issue is to contact an organism with the pharmaceutical agents in an amount and form of application so as to inhibit a tumor in its growth or prevent spreading of a tumor in an organism in the form of metastases, inhibit tumor angiogenesis, and prevent or inhibit tumor invasion, i.e., penetration of single cells into the body tissue. For example, contacting is effected orally, via injection, topically, vaginally, rectally and/or nasally.

The amount of compounds of the invention to be used in a healthy person in the event of prophylaxis or in a patient in the event of therapy is formulated and the dose established according to conventional medical practice, considering the disorder to be treated, the condition of each individual patient, the site of administration, the procedure of administration and other factors well-known to the attending physicians. Similarly, the dose of the administered compounds of the invention depends on the characteristics of the tumor, on the in vivo half-life of the compounds of the invention in plasma, and on the concentration of the compounds of the invention in the formulation, and also on the route of administration, site and rate of dosage, clinical tolerance of each individual (human and animal), pathological affection of the patient and the like, as is well-known to physicians or other persons skilled in the art. In general, dosages of about 0.1 to 1000 mg per individual and administration are preferred; particularly preferred is a dosage of from 10 to 500 mg, even more preferably 200 to 400 mg, and particularly 300 mg. It is also possible to employ varying dosages during a sequence of consecutive administrations.

In a preferred fashion, the compounds of the invention or the kit allowing provision thereof are used in a combination therapy, especially in the treatment of tumors in organisms, preferably humans or animals. The treatment of tumors comprises prophylaxis, prevention, diagnosis, attenuation, therapy, follow-up and/or aftercare of metastasizing, invasion and/or angiogenesis, said follow-up preferably being monitoring the effectiveness of an anti-tumor treatment. In a particularly preferred fashion, said combination therapy comprises a chemotherapy, a treatment with cytostatic agents and/or a radiotherapy. In a particularly preferred embodiment of the invention the combination therapy is an adjuvant, biologically specific form of therapy, and in a particularly preferred fashion, said form of therapy is an immune therapy. Furthermore, in a particularly preferred fashion the combination therapy comprises a gene therapy and/or a therapy using a compound according to the invention. Various combination therapies, especially for the treatment of tumors, are well-known to those skilled in the art. For example, a treatment with cytostatic agents or e.g. irradiation of a particular tumor area can be envisaged within the scope of a combination therapy, and this treatment is combined with a gene therapy, using the compounds of the invention as anticancer agents. Accordingly, the use of the compounds according to the invention for increasing the sensitivity of tumor cells to cytostatic agents and/or radiation can be particularly preferred. Furthermore, a preferred use of the compounds according to the invention is in inhibiting the vitality, the proliferation rate of cells and/or inducing apoptosis and cell cycle arrest.

In a preferred embodiment the cancerous disease or tumor being treated or prevented is selected from the group of cancerous diseases or tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatoses, immune suppression-related malignancies and/or tumor metastases.

More specifically, the tumors may comprise the following types of cancer: adenocarcinoma of breast, prostate and colon; all forms of lung cancer starting in the bronchial tube; bone marrow cancer, melanoma, hepatoma, neuroblastoma; papilloma; apudoma, choristoma, branchioma; malignant carcinoid syndrome; carcinoid heart disease, carcinoma (for example, Walker carcinoma, basal cell carcinoma, squamobasal carcinoma, Brown-Pearce carcinoma, ductal carcinoma, Ehrlich tumor, in situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchio-alveolar carcinoma, bronchial carcinoma, squamous cell carcinoma and transitional cell carcinoma); histiocytic functional disorder; leukemia (e.g. in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia); malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulosa cell tumor; gynadroblastoma; hidradenoma; islet-cell tumor; Leydig cell tumor; papilloma; Sertoli cell tumor, theca cell tumor, leiomyoma; leiomyosarcoma; myoblastoma; myoma; myosarcoma; rhabdomyoma; rhabdomyosarcoma; ependymoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerotizing angioma; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phylloides; hemangiosarcoma; lymphangiosarcoma; myxosarcoma, ovarian carcinoma; sarcoma (for example, Ewing sarcoma, experimentally, Kaposi sarcoma and mast cell sarcoma); neoplasms (for example, bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, of the central nervous system, neoplasms of the hearing organ, pelvis, respiratory tract and urogenital tract); neurofibromatosis and cervical squamous cell dysplasia.

In another preferred embodiment the cancerous disease or tumor being treated or prevented is selected from the group of tumors of the ear-nose-throat region, comprising tumors of the inner nose, nasal sinus, nasopharynx, lips, oral cavity, oropharynx, larynx, hypopharynx, ear, salivary glands, and paragangliomas, tumors of the lungs comprising non-parvicellular bronchial carcinomas, parvicellular bronchial carcinomas, tumors of the mediastinum, tumors of the gastrointestinal tract, comprising tumors of the esophagus, stomach, pancreas, liver, gallbladder and biliary tract, small intestine, colon and rectal carcinomas and anal carcinomas, urogenital tumors comprising tumors of the kidneys, ureter, bladder, prostate gland, urethra, penis and testicles, gynecological tumors comprising tumors of the cervix, vagina, vulva, uterine cancer, malignant trophoblast disease, ovarial carcinoma, tumors of the uterine tube (Tuba Faloppii), tumors of the abdominal cavity, mammary carcinomas, tumors of the endocrine organs, comprising tumors of the thyroid, parathyroid, adrenal cortex, endocrine pancreas tumors, carcinoid tumors and carcinoid syndrome, multiple endocrine neoplasias, bone and soft-tissue sarcomas, mesotheliomas, skin tumors, melanomas comprising cutaneous and intraocular melanomas, tumors of the central nervous system, tumors during infancy, comprising retinoblastoma, Wilms tumor, neurofibromatosis, neuroblastoma, Ewing sarcoma tumor family, rhabdomyosarcoma, lymphomas comprising non-Hodgkin lymphomas, cutaneous T cell lymphomas, primary lymphomas of the central nervous system, morbus Hodgkin, leukemias comprising acute leukemias, chronic myeloid and lymphatic leukemias, plasma cell neoplasms, myelodysplasia syndromes, paraneoplastic syndromes, metastases with unknown primary tumor (CUP syndrome), peritoneal carcinomatosis, immunosuppression-related malignancy comprising AIDS-related malignancy such as Kaposi sarcoma, AIDS-associated lymphomas, AIDS-associated lymphomas of the central nervous system, AIDS-associated morbus Hodgkin and AIDS-associated anogenital tumors, transplantation-related malignancy, metastasized tumors comprising brain metastases, lung metastases, liver metastases, bone metastases, pleural and pericardial metastases, and malignant ascites.

In another preferred embodiment the cancerous disease or tumor being treated or prevented is selected from the group comprising mammary carcinomas, gastrointestinal tumors, including colon carcinomas, stomach carcinomas, pancreas carcinomas, colon cancer, small intestine cancer, ovarial carcinomas, cervical carcinomas, lung cancer, prostate cancer, kidney cell carcinomas and/or liver metastases.

Accordingly, the invention also relates to a method for the treatment of tumors, wherein the pharmaceutical agents of the invention are contacted with an organism, said contacting preferably can be effected using capsules, anal or vaginal suppositories, tablets, ointments, creams or infusion solutions. As to the inventive method for the treatment of diseases, reference is made to the explanations relating to the use of said pharmaceutical agent or to the pharmaceutical agent itself.

Compared to well-known compounds or agents, especially cis-platinum compounds and compounds having pharmaceutical base materials other than those defined according to the invention, the pharmaceutical agents according to the invention have quite a number of advantages. Compared to cis-platinum compounds, the cis-oxoplatinum compounds of the invention can be employed in a wider range of concentrations. Also, the lethal dose of cis-oxoplatin is proportionally much higher than that of cis-platinum compounds. Potency and effectiveness of cis-oxoplatin with respect to particular types of tumors are higher than that of cisplatin.

Thus, for example, it has been demonstrated that some forms of prostate cancer resistant to cis-platinum compounds show advantageous effects when treated with cis-oxoplatin. Furthermore, the nephrotoxic effect of cis-oxoplatin is much lower compared to cisplatin, and the anti-metastatic effect of cis-oxoplatin is higher than that of cisplatin. Among other things, this has its cause in that cis-oxoplatinum compounds, due to their different spatial structure, interact with DNA molecules in a different way, for example. Thus, for example, binding of selected cis-platinum compounds to DNA molecules is based on internal substitution of chlorine ligands, whereas binding of cis-oxoplatin to DNA molecules is based on the formation of hydrogen bridges. In the body of a patient, human or animal, cis-oxoplatinum compounds show a largely inert behavior. For this reason, they can be employed at higher concentrations than cis-platinum compounds, with no toxic side effects. Another remarkable feature of the pharmaceutical agents comprising cis-oxoplatin is their antitumor effectiveness against virtually any type of tumor. Especially in the liver and kidneys, the pharmaceutical agents of the invention have a shorter half-life than pharmaceutical agents based on cis-platinum compounds. More advantageously, the agents of the invention exhibit very good effect when administered orally, because they enter the systemic circulation in the body very quickly, resulting in a marked increase of their antitumor activity, which is seen e.g. in a reduction of the tumor size. Furthermore, the ointments, creams and gels according to the invention can be used with very good success in a topical chemotherapy. In such a topical chemotherapy, the inventive ointment, cream or gel or powder is directly applied on the surface of the skin. This can also make sense in those cases where a tumor has not yet formed, but some pre-forms, such as acrokeratosis, have already become manifest. Such a use is particularly advantageous because side effects possibly occurring do not affect the entire organism. Advantageously, the skin is capable of absorbing the pharmaceutical agents of the invention in the form of a depot; that is, the half-life inside the skin of the active substance of the agent according to the invention is approximately 12 days. In a preferred fashion, the pharmaceutical agents of the invention can also be used in an intraperitoneal chemotherapy. In particular, abdominal tumor diseases are treated by means of this therapy. Such chemotherapies can be combined with a hyperthermal intraperitoneal chemotherapy, for example. The resulting hyperthermal effects allow more sensitive action of the pharmaceutical agents of the invention on tumors. In particular, the intraperitoneal chemotherapy can be used in case of ovarian carcinoma.

Without intending to be limiting, the invention will be explained in more detail with reference to the following examples.

DESCRIPTION OF VARIOUS AND PREFERRED EMBODIMENTS OF THE INVENTION

1. Use of Cis-Diammoniumdichlorodihydroxoplatinum(IV) and Salts Thereof

Growth inhibition tests on various human cell lines show the different activities of cisplatin, cis-oxoplatin and oxaliplatin. The results illustrated below show that cis-oxoplatin has an activity similar to that of oxaliplatin, but higher activity than carboplatin. The following Table illustrates the results produced with cisplatin, oxoplatin, carboplatin and oxaliplatin (the values specified are $IC_{50}$ values in μg/ml, i.e., the concentration where 50% of the cells survive, nd=not determined; res=resistant=non-sensitive or $IC_{50}$ value cannot be determined at a concentration of up to 40 μg/ml; IC=inhibition concentration).

TABLE 1

| Cell line | Cis-platin | cis-Oxoplatin | Carboplatin | Oxaliplatin |
| --- | --- | --- | --- | --- |
| HOS Osteosarcoma | nd | 2.5 | 5 | nd |
| SaOS Osteosarcoma | nd | 5 | 5 | nd |
| PC3 Prostate | res | 7.5 | 10 | nd |
| M607 Melanoma | 0.3 | 5 | 10 | 10 |
| M518 Melanoma | 40 | res | res | res |
| Me128 Melanoma | 0.3 | 2.5 | 10 | 10 |
| JVSO Melanoma | 40 | 10 | res | res |
| Panc1 Pancreatic cancer | 1 | 40 | 20 | 5 |
| BxPC3 Pancreatic cancer | 0.6 | 2.5 | 10 | 10 |
| MiaPaCa2 Pancreatic cancer | 1.5 | 5 | 5 | 5 |
| HCT8 Colon carcinoma | 5 | 40 | res | res |
| HT29 Colon carcinoma | 0.3 | 20 | 20 | 20 |
| HCT-15 Colon carcinoma | 0.3 | 20 | res | 10 |
| A498 Renal cells | 1 | 20 | res | 10 |
| C320DM Colon carcinoma | 0.3 | 2.5 | 10 | 0.15 |
| Colo205 Colon carcinoma | 10 | res | res | 1 |
| CC1227 Colon carcinoma | 0.3 | 10 | res | 0.2 |
| MCF-7 Breast cancer | 2.5 | 5.5 | res | res |
| T47D Breast cancer | 0.3 | 2.5 | nd | 0.1 |

TABLE 2

| | $IC_{50}$ μg/ml | |
| --- | --- | --- |
| Cell line | cis-Oxoplatin | cis-Oxoplatin sodium salt |
| T47D Breast cancer | 3 | 18 |
| SK-OV3 Ovarian cancer | 15 | 22 |
| U 373 MG Astrocytoma | 15 | 18 |
| BxPC3 Pancreatic carcinoma | 13 | 12 |
| SK-OV4 Ovarian cancer | 16.2 | 12.8 |
| PC3 Prostate | 7.5 | 5.3 |
| CaCo-2 Colon | 1.52 | 2.22 |
| CRO2B Carcinoid | 3.0 | 10.1 |
| HT29 Colon | 13.5 | 4.55 |
| Du145 Prostate | 19.0 | 27.0 |
| SW480 Colon | 8.2 | 2.5 |
| SIM Sarcoma | 15.2 | 11.2 |

The activities differ according to the cell line. The Na salt is clearly more effective (about 70%) with HT29 and SW480 and more effective with SK-OV4, PC3 and SIM (about 30%), and less efficient with CaCo-2, DU145 and CRO2B cells. The $IC_{50}$ values of these cells are therefore 10.5±6.4 μg/ml for oxoplatin versus 9.5±8 μg/ml for the sodium salt.

The results determined show that chemically highly similar platinum compounds such as cisplatin and cis-oxoplatin have different effects on various human cancer cells, and that the salts of the platinum compounds show a behavior on tumors which is different from that of the base compounds from which the salts have been generated. In general, and extending beyond concrete tests, it appears that the DNA binding ability of cis-oxoplatin salts, especially of cis-oxoplatin sodium salt, is unexpected when compared to cis-oxoplatin. For example, this may have its cause in the different structures of the DNA adducts formed with the base, on the one hand, and with the salt, on the other hand. Furthermore, it can be assumed that the cis-oxoplatin salts undergo a different process of biotransformation compared to the corresponding bases. These unexpected variations are of great importance when using bases and salts in tumor therapy. For example, further important issues of such different behavior of bases and salts are: absorption, diffusion and distribution in the tissue and in particular organs. The intracellular uptake and the toxicity of cis-oxoplatin sodium salts are different from those of the corresponding base; the absorption and dissolution, as well as the pharmacogenetics of cis-oxoplatin salts are not comparable to those of the base. The type of interaction with DNA, and the efficiency and effectiveness, as well as the therapeutic potency of cis-oxoplatin salts are different from those of cis-oxoplatin. Inter alia, this can be demonstrated on the chemical structure of cis-oxoplatin calcium salt as one example of salts of bivalent cations:

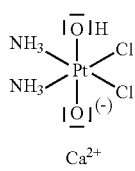

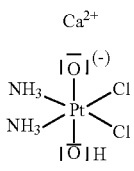

As can be seen in this structure, salts such as calcium salts have a structure that is completely different from that of the corresponding base. Such variations in the stereochemical properties result in a different behavior with respect to the interaction with DNA in cells, especially in cancer cells. As a result of the different structure of salts, a lower dose can be sufficient to achieve a therapeutic effect. Furthermore, biotransformation may result in conversion of platinum(IV) complexes into platinum(II) complexes in the body, and platinum(IV) and platinum(II) complexes have different effects on different tumors (see Table 1).

2. Cytotoxic Activity of Trans-Oxoplatin (TRAXO)

trans-Oxoplatin was tested on a panel of cell lines, using double steps and an initial concentration of 40 µg/ml. As the $IC_{50}$ values were not reached in most cases, cell survival at the highest concentration is indicated.

TABLE 3

| Cell line | | % Survival with 40 µg/ml TRAXO (unless 20 µg/ml indicated) |
|---|---|---|
| U-87-MG | Astrocytoma | 100 |
| ASTRO | Astrocytoma | 82(20)/71 |
| SW620 | Colon carcinoma | 43/51/97 |
| MDA-MB-231 | Breast cancer | 70/103/106 |
| G-292 | Osteosarcoma | 8.6/68 |
| PANC1 | Pancreatic cancer | 100 |
| CRO1A | Carcinoid | 87/104/70 |
| CRO2B | Carcinoid | 24/57 |
| MIAPaCa2 | Pancreatic Cancer | 92/83 |
| Fib3 | Fibroblasts | 91 |
| K562 | Leukemia | 97 |
| WI-38 | Embryonic lung fibroblasts | 21 |
| COLO 205 | Colon carcinoma | 109 |
| HCT-15 | Colon carcinoma | 100 |
| T-47D | breast cancer | 101 |
| HL-60 | Leukemia | 0.5 |
| HOS | Osteosarcoma | 4.3 |
| ACHN | Renal carcinoma | 48 |
| BxPC3 | Pancreatic carcinoma | 106 |

As shown by the tests on 19 cell lines, TRAXO has considerable activity against a colon carcinoma cell line (SW 620), against 2 osteosarcoma cell lines (G-292, HOS), against a renal carcinoma cell line (ACHN), a leukemia cell line (HL-60), and against an embryonic pulmonary fibroblast cell line (WI-38). Cell lines sensitive to cis-oxoplatin, such as T-47D and BxPC3, are non-sensitive to TRAXO. The salts of the trans-oxoplatin compounds may have a different therapeutic potential and different effectiveness against particular human cancer cells, cell lines and tumors.

Comparison of the Effect of Cis-Oxoplatin and Cis-Oxoplatin Ca Salt

The effect of cis-oxoplatin Ca and cis-oxoplatin was compared on 10 cell lines (Table 4).

($IC_{50}$ values specified in µg/ml; the test was performed as a formazan test).

TABLE 4

| Cell line | Origin | Oxoplatin $IC_{50}$ (µg/ml) | Oxoplatin Ca $IC_{50}$ (µg/ml) |
|---|---|---|---|
| SW480 | Colon | 8.2 | 2.5 |
| MDA-MB-435 | Breast | 16.5 | 12.0 |
| BT20 | Breast | 3.75 | 3.5 |
| Colo205 | Colon | 29.0 | 13.5 |
| Du145 | Prostate | 19.0 | 14.5 |
| HT29 | Colon | 13.5 | 8.0 |
| CRO2B | Carcinoid | 3.0 | 2.20 |
| CaCo-2 | Colon | 1.52 | 0.87 |
| BxPC3 | Pancreas | 26.0 | 30.0 |
| T47D | Breast | 2.5 | 3.6 |

The $IC_{50}$ (±SEM) mean value of cis-oxoplatin for all cell lines is 12.3±3.2, compared to cis-oxoplatin Ca with an $IC_{50}$ value (±SEM) of 9.1±2.8.

The following comparison shows the dose-response dependence for cis-oxoplatin versus cis-oxoplatin Na in PC3 cells:

| Conc. (µg/ml) | % Survival/oxoplatin | % Survival/Na salt |
|---|---|---|
| 40 | 15.8 ± 2.7 | 0.6 ± 0.5 |
| 20 | 56.7 ± 6.3 | 33.2 ± 3.0 |
| 10 | 87.4 ± 11.8 | 77.7 ± 2.4 |
| 5 | 105.2 ± 10.8 | 109.3 ± 9.1 |

These are typical results for PC3, SK-OV4 and SIM. The Na salt is more active at higher concentration ranges; the differences are smaller at lower concentrations. Presumably, cis-oxoplatin Na has a slightly different structure or a different mechanism of action compared to oxoplatin, so that it is 30 to 70% more active or 40 to 50% less active than cis-oxoplatin in particular cell lines. The superior activity of cis-oxoplatin Na appears to be present at higher concentration ranges (above 5 µg/ml).

3. Therapeutic Effect of the Ointments, Infusion Solutions and Tablets According to the Present Patent Application In a first test series, tablets, ointments and infusion solutions were tested on various tumor rats developing both internal and external tumors. The other drugs according to the invention were tested in additional, subsequent test series. Following combining of cis-oxoplatin and base material, the tablet included 50 mg of cis-oxoplatin, 39.5 mg of lactose, 2.5 mg of corn starch, 2.5 mg of poly(O-carboxymethyl)starch sodium salt, 2.5 mg of calcium hydrogen phosphate×$2H_2O$, 2.5 mg of cellulose powder, and 0.5 mg of magnesium stearate. Following contacting cis-oxoplatin with base material, the ointment included 50 mg of cis-oxoplatin, 120 mg of propylene glycol, 5.5 mg of Macrogol stearate 1000, 22 mg of cetyl stearyl alcohol, and 851.5 mg of VASELINE retrolatum. In a preparation of 5 mg/ml solution, the infusion solution included 5 mg of cis-oxoplatin, 9 mg of benzyl alcohol, 2 mg of Polysorbate 80, 650 mg of 70% sorbitol solution, and 500 mg of water.

All drugs were provided about 30 min to one hour prior to application by mixing the cis-oxoplatin active substance with the base material.

The tablets were administered in the form of a feed admixture. Infusion of the infusion solution was effected according to common laboratory practice via infusion tube. The ointment was applied on those areas of the back which exhibited degenerate tissue.

Tumor effectiveness was established by weight determination and measuring the outer areas of degenerate tissue. As a comparison, the tumor effectiveness was also tested using an infusion solution comprising oxoplatin in sodium chloride solution and by means of direct oral administration of oxoplatin and by applying oxoplatin powder placed on the tumor area on the back of the laboratory animal by means of a bandage. Furthermore, tablets comprising cis-oxoplatin and sodium hydrogen carbonate or sodium alginate were tested.

Administration of pure oxoplatin with no base materials defined according to the invention resulted in a reduction of tumor growth. However, irritations in the surrounding tissue caused by pure oxoplatin could be seen, and also, the oxoplatin was rapidly eliminated. The tablets comprising cis-oxoplatin and sodium hydrogen carbonate and sodium alginate resulted in formation of edema in rats. Presumably, formation of carbon dioxide by HCl in the gastric juice and hydrogen carbonate resulted in an enlargement of the plasma volume. Enlargement of the plasma volume causes elevated blood pressure and formation of edema. As platinum complexes can be toxic to the kidneys, formation of edema also promotes renal insufficiency. The tested drugs claimed according to the invention do not show such drawbacks. In particular, the use of salts of cis-oxoplatin results in further improvement of the antitumor effectiveness. The comparative substances either have more side effects or inferior antitumor effectiveness when compared to the drugs according to the invention. The results obtained with other drugs according to the invention are comparable with those of the tablets, ointments and infusion solutions. Compositions explicitly disclosed were employed.

What is claimed is:

1. A pharmaceutical agent consisting of:
   (1) cis-diammoniumdichloro-trans-dihydroxoplatinum (IV) (cis-oxoplatin) and/or salts thereof, and
   (2) a base material selected from a tablet, a capsule, and a coated tablet, wherein said base material and the cis-diammoniumdichloro-trans-dihydroxoplatinum(IV) are:
      a capsule consisting of cis-oxoplatin:silicon dioxide: mannitol or magnesium stearate at a ratio of 0.1 to 10:0.1 to 10:0.1 to 10;
      a tablet consisting of cis-oxoplatin:lactose:corn starch: poly(O-carboxymethyl)starch sodium salt:calcium hydrogen phosphate×2H$_2$O:cellulose powder:magnesium stearate at a ratio of 10 to 500:20 to 150:1 to 10:1 to 10:1 to 10:1 to 10:0.1 to 7; and
      a tablet consisting of cis-oxoplatin silicon dioxide magnesium stearate at a ratio of 0.1 to 10:0.1 to 10:0.1 to 10.

2. A pharmaceutical agent consisting of:
   (1) cis-diammoniumdichloro-trans-dihydroxoplatinum (IV) (cis-oxoplatin) and/or salts thereof, and
   (2) a base material, wherein said base material and the cis-diammoniumdichloro-trans-dihydroxoplatinum (IV) are:
      a capsule consisting of cis-oxoplatin:silicon dioxide: mannitol or magnesium stearate at a ratio of 0.1 to 10:0.1 to 10:0.1 to 10, and additionally silicon dioxide and mannitol or silicon dioxide and magnesium stearate and/or pharmaceutically acceptable vehicles.

3. A pharmaceutical agent consisting of:
   (1) cis-diammoniumdichloro-trans-dihydroxoplatinum (IV) (cis-oxoplatin) and/or salts thereof, and
   (2) a base material, wherein said base material and the cis-diammoniumdichloro-trans-dihydroxoplatinum (IV) are:
      a capsule consisting of cis-oxoplatin:silicon dioxide: mannitol or magnesium stearate at ratio of 0.1 to 10:0.1 to 10:0.1 to 10, wherein
   the capsule consists 50 mg of silicon dioxide, 50 mg of mannitol or 50 mg of magnesium stearate and 50 mg of oxoplatin, or, alternatively, 50 mg of cis-oxoplatin, 39.5 mg of lactose or 39 mg, 2.5 mg or 2 mg of corn starch, 2.5 mg of poly(O-carboxymethyl)starch sodium salt, 2.5 mg of calcium hydrogen phosphate×2H$_2$O, 2.5 mg of cellulose powder, and 0.5 mg of magnesium stearate, or, alternatively, 50 mg of cis-oxoplatin, 50 mg of silicon dioxide and 50 mg of magnesium stearate.

4. A pharmaceutical agent consisting of:
   (1) cis-diammoniumdichloro-trans-dihydroxoplatinum (IV) (cis-oxoplatin) and/or salts thereof, and
   (2) a base material, wherein said base material and the cis-diammoniumdichloro-trans-dihydroxoplatinum (IV) are:
      a tablet consisting of cis-oxoplatin:silicon dioxide:mannitol or magnesium stearate at a ratio of 0.1 to 10:0.1 to 10:0.1 to 10, wherein the tablet consists 50 mg of cis-oxoplatin, 39.5 mg of lactose, 2.5 mg of corn starch, 2.5 mg of poly(O-carboxymethyl)starch sodium salt, 2.5 mg of calcium hydrogen phosphate× 2H$_2$O, 2.5 mg of cellulose powder and 0.5 mg of magnesium stearate, or, alternatively, 50 mg of cis-oxoplatin, 50 mg of silicon dioxide and 50 mg of magnesium stearate.

5. The pharmaceutical agent of claim 2, wherein the or pharmaceutically acceptable vehicles are siosomes, liposomes and/or nanocapsules.

6. A kit comprising (1) and (2) of the pharmaceutical agent of claim 1, 2, 3, or 4 in separate containers.

7. The kit of claim 6, wherein the kit is a chemotherapeutic kit.

* * * * *

UNITED STATES PATENT AND TRADEMARK OFFICE
CERTIFICATE OF CORRECTION

PATENT NO. : 7,749,534 B2
APPLICATION NO. : 10/595399
DATED : July 6, 2010
INVENTOR(S) : Salama It is certified that error appears in the above-identified patent and that said Letters Patent is hereby corrected as shown below:

Col. 3 line 8 delete "retrolatum", should read-- petrolatum

Col. 11 line 48 delete "retrolatum", should read-- petrolatum

Col. 11 line 55 delete "retrolatum", should read-- petrolatum

Col. 14 line 23 delete "retrolatum", should read-- petrolatum

Col. 22 line 63 delete "retrolatum", should read-- petrolatum

Signed and Sealed this
Twenty-eighth Day of June, 2011

David J. Kappos
*Director of the United States Patent and Trademark Office*